United States Patent [19]

Mees et al.

[11] 4,454,075

[45] Jun. 12, 1984

[54] PROCESS FOR REMOVING SULFURIC ACID FROM THE REACTION MIXTURE OBTAINED IN THE SULFOXIDATION OF PARAFFINS

[75] Inventors: Bernhard Mees, Charlotte, N.C.; Herbert Ramloch, Bad Soden am Taunus, Fed. Rep. of Germany

[73] Assignee: Hoechst Aktiengesellschaft, Fed. Rep. of Germany

[21] Appl. No.: 471,805

[22] Filed: Mar. 3, 1983

[51] Int. Cl.$^3$ .................................... C07C 143/02
[52] U.S. Cl. ................................. 260/513 R
[58] Field of Search ................................. 260/513 R

[56] References Cited

U.S. PATENT DOCUMENTS

| 2,316,670 | 4/1943 | Colgate et al. | 260/513 R |
|---|---|---|---|
| 3,454,479 | 7/1969 | Hopkins et al. | 260/513 R |
| 3,481,849 | 12/1969 | Beermann et al. | 260/513 R |
| 3,518,299 | 6/1970 | Alston | 260/513 R |
| 3,577,456 | 5/1971 | Kleiner et al. | 260/513 R |
| 3,660,471 | 5/1972 | Sawano et al. | 260/513 R |
| 3,666,797 | 5/1972 | Nagayama et al. | 260/513 R |
| 3,743,673 | 7/1973 | Downer et al. | 260/513 R |
| 3,926,757 | 12/1975 | Rosinger | 260/513 R |
| 4,233,236 | 11/1980 | Kern et al. | 260/513 R |
| 4,321,215 | 3/1982 | McAbery | 260/513 R |

*Primary Examiner*—Alan Siegel
*Attorney, Agent, or Firm*—Connolly and Hutz

[57] ABSTRACT

A process for removing sulfuric acid from the reaction mixture obtained in the sulfoxidation of paraffins, which comprises adding an organic amine sulfate to the reaction mixture and removing the phase consisting of water and sulfuric acid which thereby separates out, adding to the remaining phase containing alkanesulfonic acid and alkanesulfonic acid amine salt an amount of an alkali metal hydroxide sufficient to convert the alkanesulfonic acid and the alkanesulfonic acid amine salt into the alkali metal alkanesulfonate, the organic amine being liberated, removing the paraffin from this mixture, together with the free organic amine, by steam distillation, removing the free organic amine from the paraffin by extraction with sulfuric acid and employing the resulting organic amine sulfate again at the start of the whole process for removing the sulfuric acid.

3 Claims, No Drawings

PROCESS FOR REMOVING SULFURIC ACID FROM THE REACTION MIXTURE OBTAINED IN THE SULFOXIDATION OF PARAFFINS

In the sulfoxidation of linear paraffins by the light-/water method, i.e. with $SO_2$ and $O_2$ in the presence of water and using UV light, a mixture of paraffin, water, alkanesulfonic acid and sulfuric acid is formed after the undissolved paraffin has been removed. The composition of this mixture depends on the chain length of the paraffin employed. For example, in the sulfoxidation of a paraffin having a chain length of 12–18 carbon atoms and a maximum at 14–17 carbon atoms, a mixture having approximately the following composition is obtained after the $SO_2$ has been expelled: 37.5% of water, 32% of paraffin, 23% of alkanesulfonic acid and 7.5% of sulfuric acid.

This mixture is a completely clear solution and will be called the extract in the text which follows. It is probably a microemulsion of paraffin in the aqueous sulfuric acid, the alkanesulfonic acid acting as a solubilizing agent.

The isolation of the pure Na alkanesulfonate, which is of great significance as a readily biologically degradable surfactant, is greatly impeded by the presence of sulfuric acid since a corresponding amount of sodium sulfate is formed during the neutralization.

In the past, therefore, attempts have repeatedly been made to influence the extract such that the sulfuric acid is removed. Thus, for example, it is known that part of the sulfuric acid is removed if the extract is warmed to about 90° C. However, removal of only about 35% of the total amount of $H_2SO_4$ can be achieved industrially. The addition of weakly polar alcohols having not less than 5 carbon atoms to the extract in order to cause demixing into an organic phase which contains all the sulfonic acid and an aqueous phase which contains almost all the sulfuric acid is also known. The disadvantages of this process are, on the one hand, the large amount of alcohol which must be added to the extract (between 20 and 80 g of alcohol per 100 g of extract) and, on the other hand, the difficulty of separating the alcohol from the paraffin. Finally, the addition of weakly polar organic solvents, such as ethers, ketones, esters and aliphatic keto esters to the extract is known. The disadvantage of this process is also the large amount of solvents required for removing the sulfuric acid. According to the literature, the amount of solvents used is 30–100 g per 100 g of extract.

There was thus the object of achieving as far as possible quantitative removal of the sulfuric acid with the addition of as little as possible auxiliary. We have now found that this object can be achieved by adding an organic amine salt to the reaction mixture obtained in the sulfoxidation of paraffins.

The invention thus relates to a process for removing sulfuric acid from the reaction mixture obtained in the sulfoxidation of paraffins, which comprises adding an organic amine sulfate to the reaction mixture and removing the phase consisting of water and sulfuric acid which thereby separates out, adding to the remaining phase containing alkanesulfonic acid and alkanesulfonic acid amine salt an amount of an alkali metal hydroxide sufficient to convert the alkanesulfonic acid and the alkanesulfonic acid amine salt into the alkali metal alkanesulfonate, the organic amine being liberated, removing the paraffin from this mixture, together with the free organic amine, by steam distillation, removing the free organic amine from the paraffin by extraction with sulfuric acid and employing the resulting organic amine sulfate again at the start of the whole process for removing the sulfuric acid.

Sulfates of organic amines of the formula

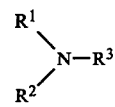

in which $R^1$ denotes $C_3$–$C_{18}$-alkyl, $C_5$–$C_8$-cycloalkyl, phenyl, which can be substituted by 1 to 3 $C_1$–$C_4$-alkyl groups or one $C_1$–$C_9$-alkyl group, or, if $R^3$ represents a group of the formula $-X-NR^1R^2$, also hydrogen, $R^2$ has the same meaning as $R^1$ and additionally denotes hydrogen, $R^3$ has the same meaning as $R^1$ and additionally denotes hydrogen or a group of the formula $-X-NR^1R^2$, and X denotes phenylene or $C_8$–$C_{12}$-alkylene, are preferably used for the removal of the sulfuric acid. Amines of the above formula which contain only alkyl or alkylene groups, in particular straight-chain alkyl or alkylene groups, are particularly preferred.

Suitable amines of this type are aliphatic mono-, di- and tri-alkylamines, in which the alkyl radicals can be either straight-chain or branched. Corresponding cycloaliphatic mono-, di- and tri-alkylamines are also suitable. Aromatic amines, such as, for example, xylidine or ethylaniline, also display the desired effect, as do longer-chain aliphatic diamines.

The amine sulfates of the following amines display a particularly good activity: hexylamine, heptylamine, octylamine, diisobutylamine, dibutylmethylamine, tripentylamine, trihexylamine, cyclohexylamine, dicyclohexylamine, tricyclohexylamine, diaminooctan-1,8-aniline, o-toluidine, p-toluidine, xylidine, 2-ethylaniline, o-diaminobenzene, aminodiphenyl and p-nonylaniline.

The process according to the invention is distinguished by the fact that an aqueous solution of an organic amine sulfate is obtained at the end of the entire process, and that this amine sulfate can be used again at the start of the process. It goes without saying that the corresponding free amine can also be used, instead of the amine sulfate, in order to set this circulatory process in motion for the first time.

These amines, or the corresponding sulfates, are added in an amount of 1 to 5, preferably 2 to 4, parts by weight, calculated as the free amine, per 100 parts by weight of the crude sulfonation mixture (extract). The extract is first freed from residual amounts of $SO_2$ still dissolved therein. Deposition of the lower phase of water and sulfuric acid by addition of the amine or amine sulfate already takes place at room temperature. In order to achieve as far as possible complete removal of the sulfuric acid, it is advantageous to heat the extract to about 20° to 130° C., in particular 90° to 95° C. After the amine sulfate or amine has been added, the mixture is left to stand for about another 30 to 60 minutes and the lower phase formed, which consists of about 20% strength aqueous sulfuric acid and contains virtually the entire amount of sulfuric acid originally present in the extract, is removed. This sulfuric acid can be further worked up in a separate process. The upper phase which remains consists of the unreacted residual paraffin and the alkanesulfonic acid, some of this alkanesulfonic acid being in the form of its salt with the amine added as the phase-separating agent. Since, in practice, a pure Na alkanesulfonate is required, there was the object of removing the amine employed quantitatively from the sulfonate and to work it up economically such that it can be used for a further removal of sulfuric acid from the extract.

For this purpose, the number of moles of sodium hydroxide corresponding overall to the molar amount of free alkanesulfonic acid and alkanesulfonic acid amine salt is first added to the upper phase which is obtained after removal of the sulfuric acid and contains the paraffin, free alkanesulfonic acid and alkanesulfonic acid amine salt.

This is achieved by adding sodium hydroxide solution until the pH value corresponds to the pH value shown by the free amine by itself in aqueous solution (for example pH 10.5 in the case of tributylamine). The amine is thereby displaced, by the sodium hydroxide solution, from salt formation with the alkanesulfonic acid and is liberated. This mixture is then subjected to steam distillation (stripping) up to a temperature of about 250° C., the paraffin still present being removed, together with the free organic amine. This temperature of 250° C. is as a rule sufficient to lower the residual paraffin content in the alkanesulfonate to below 1%. The amine sulfate or amine is chosen such that the boiling point of the free amine is not more than 300° C., and is preferably between 150° and 250° C. These two measures, namely maintaining the pH value in the manner described and choosing an amine with a suitable boiling point, ensure that the amine or amine salt can no longer be detected in the end product after working up.

For reasons of cost, the stripped paraffin must be fed directly again to the sulfoxidation. It contains the entire organic amine; the stripping water itself still contains only traces of amine (less than 0.1% by weight), since the amine is extracted from the water by the paraffin.

However, so that the sulfoxidation of the paraffin is not made more difficult, the paraffin must be separated from the amine.

This is effected by adding some of the approximately 20% strength sulfuric acid removed at the start of the entire process to the mixture of organic amine and paraffin.

This extraction of the amine from the paraffin is carried out industrially by metering the aqueous sulfuric acid into the paraffin, via a mixer, and then removing pure paraffin as the upper phase and the amine salt solution as the lower phase via a downstream separator. The amount of sulfuric acid is variable. The upper limit is a ratio of 1 mole of sulfuric acid (100% strength) per 2 moles of amine in the paraffin. However, if desired, it is possible to meter in much more sulfuric acid than there is amine present. For reasons of a favorable space/time yield, however, a ratio of 1 mole of sulfuric acid (100% strength) per 1.5–1.8 moles of amine in the paraffin, or 10 to 40% by weight of 20% strength sulfuric acid, based on the paraffin/amine mixture, will be chosen. The paraffin thus purified still contains less than 0.1% of amine and can be recycled to the sulfoxidation.

The other phase, which consists of the aqueous solution of the organic amine sulfate containing sulfuric acid, is used again for removing the sulfuric acid from the extract. This acidic amine salt solution is metered into the fresh extract in an amount such that the optimum ratio of extract to amine (calculated as free amine) described above results.

It has been found, surprisingly, that this amount of sulfuric acid which is introduced into the extract again by addition of the organic amine in the form of the sulfate is likewise removed quantitatively again in the course of the entire removal process. The amines or amine salts are thus capable of removing sulfuric acid from the extract, independently of whether they are used as the free base or in the form of their salts. After addition of the amines or amine salts, the upper phase of the extract still contains only a small residual amount of sulfuric acid (about 1–2%), which depends solely on the amount of amine employed and not on the amount of sulfuric acid introduced beforehand by the amine sulfate. It is thus possible to recycle the amine, as described above, without troublesome and expensive separation operations, the losses being negligibly small.

Overall, the process according to the invention is particularly distinguished by the fact that complete removal of the sulfuric acid is achieved, but the amount of amine required for this is smaller than the amount of weakly polar solvents hitherto used for this purpose by a factor of about 10. The process is particularly used for separating crude sulfonation mixtures which originate from the sulfoxidation of n-paraffins having 7 to 30, preferably 10 to 20, carbon atoms.

EXAMPLE 1

9 parts by weight of di-n-pentylamine are added to 300 parts by weight of a degassed extract composed of 37.5% of water, 32% of paraffin, 23% of alkanesulfonic acid and 7.5% of sulfuric acid at 95° C., while stirring, and stirring is continued for 5 minutes. The mixture is then kept in a heated separating funnel for about 45 minutes, during which the extract separates into two phases. The colorless aqueous sulfuric acid is then drained off, as the lower phase. 105 parts by weight of an approximately 20% strength sulfuric acid, the content of which is determined by titrimetry, are obtained. 92% of the sulfuric acid present in the extract is removed.

204 parts by weight of a mixture of 14.6% of water, 47% of paraffin and 33.6% of alkanesulfonic acid, 0.057 mole percent of which is in the form of the di-n-pentylamine salt, are obtained as the upper phase. This mixture is brought to pH 12.0 with about 25 parts by weight of 50% strength by weight sodium hydroxide solution and is then subjected to stripping with superheated steam (280°–300° C.) up to an internal temperature of 250° C.

The stripped paraffin (about 105 parts by weight) is separated from the stripping water via a separator and is then extracted by shaking with about 18 parts by weight of the 20% strength sulfuric acid removed beforehand (molar ratio of $H_2SO_4$:amine = 1:1.58). After a separation time of about 5 minutes, the aqueous lower phase is drained off and the content of di-n-pentylamine in the sulfuric acid is determined analytically. It is found that, within the accuracy of measurement, the 9 parts by weight of amine employed were recovered quantitatively in the sulfuric acid phase. The resulting 24 parts by weight of sulfuric acid di-n-pentylamine salt in water are added again to 300 parts by weight of an extract having the above composition and the mixture is worked up again as described above. About 120 parts by weight of an approximately 20% strength sulfuric acid is now obtained, the residual content of sulfuric acid in the upper phase corresponding to the content on addition of pure di-n-pentylamine.

EXAMPLE 2

9 parts by weight of tri-n-butylamine are added to 300 parts by weight of an extract according to Example 1 and the mixture is further worked up according to Example 1.

After the aqueous sulfuric acid has been removed, about 210 parts by weight of the upper phase are obtained, and are brought to pH 10.5 with 25.5 parts by weight of 50% strength sodium hydroxide solution. The paraffin and the amine liberated are then stripped off and removed from the stripping water. About 105 parts by weight of paraffin+amine are obtained, and are extracted by shaking with 14 parts by weight of the 20% strength sulfuric acid removed beforehand (molar ratio of $H_2SO_4$ to amine=1:1.73). After a short phase separation time, the lower phase is drained off and the content of tri-n-butylamine in the sulfuric acid is determined. It is again found that virtually all of the tributylamine has been recycled into the aqueous sulfuric acid. As described in the preceding example, this solution can be re-used directly for a further working up of extract.

EXAMPLE 3

16 parts by weight of di-n-butylamine are added to 300 parts by weight of an extract according to Example 1 and the sulfuric acid is removed, as described above. 214 parts by weight of an upper phase containing all the alkanesulfonic acid is obtained. This upper phase is brought to pH 12 with 25.8 parts by weight of 50% strength sodium hydroxide solution and stripped with superheated steam.

About 110 parts by weight of a mixture of paraffin and dibutylamine are obtained, and are extracted by shaking with 35 parts by weight of 20% strength sulfuric acid (molar ratio of $H_2SO_4$:amine=1:1.77). In this case also, analysis shows that the dibutylamine has been transferred quantitatively to the sulfuric acid phase.

The present examples illustrate the batchwise procedure. The process according to the invention can, of course, also be carried out by a continuous procedure, in which case the advantages are even more clearly visible.

We claim:

1. A process for removing sulfuric acid from the reaction mixture obtained in the sulfoxidation of paraffins, which comprises adding an organic amine sulfate to the reaction mixture and removing the phase consisting of water and sulfuric acid which thereby separates out, adding to the remaining phase containing alkanesulfonic acid and alkanesulfonic acid amine salt an amount of an alkali metal hydroxide sufficient to convert the alkanesulfonic acid and the alkanesulfonic acid amine salt into the alkali metal alkanesulfonate, the organic amine being liberated, removing the paraffin from this mixture, together with the free organic amine, by steam distillation, removing the free organic amine from the paraffin by extraction with sulfuric acid and employing the resulting organic amine sulfate again at the start of the whole process for removing the sulfuric acid.

2. The process as claimed in claim 1, wherein the amine sulfate is used in an amount of 1 to 5 parts by weight, calculated as the free amine, per 100 parts by weight of extract.

3. The process as claimed in claim 1, wherein an amine with a boiling point of up to 300° C. is used.

* * * * *